US007873143B2

(12) United States Patent
Dunham et al.

(10) Patent No.: US 7,873,143 B2
(45) Date of Patent: Jan. 18, 2011

(54) SLIDING SAMPLE CELL INSERTION AND REMOVAL APPARATUS FOR X-RAY ANALYZER

(75) Inventors: Daniel L. Dunham, Averill Park, NY (US); James B. Quinn, Ravena, NY (US); Brian W. Gallagher, Guilderland, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 99 days.

(21) Appl. No.: 12/326,123

(22) Filed: Dec. 2, 2008

(65) Prior Publication Data

US 2009/0141862 A1 Jun. 4, 2009

Related U.S. Application Data

(60) Provisional application No. 61/005,213, filed on Dec. 3, 2007.

(51) Int. Cl.
*G01N 23/22* (2006.01)

(52) U.S. Cl. .............................. 378/79; 378/46; 378/47

(58) Field of Classification Search .................. 378/46, 378/47, 79
See application file for complete search history.

(56) References Cited

U.S. PATENT DOCUMENTS 3,462,598 A * 8/1969 Burke et al. .................. 378/47
4,263,510 A * 4/1981 Ciccarelli et al. ............. 378/46
4,303,858 A 12/1981 Oestrup
4,634,866 A 1/1987 Conway
4,698,210 A 10/1987 Solazzi
4,988,872 A * 1/1991 Nagatsuka et al. ............. 850/9
5,253,280 A * 10/1993 Mizuta ........................ 378/45
5,323,441 A * 6/1994 Torrisi et al. .................. 378/44
5,351,281 A * 9/1994 Torrisi et al. .................. 378/79
5,454,020 A 9/1995 Solazzi
5,497,008 A * 3/1996 Kumakhov .............. 250/505.1

(Continued)

FOREIGN PATENT DOCUMENTS

WO WO2007/054718 A 5/2007

OTHER PUBLICATIONS

International Search Report and Written Opinion from International Application No. PCT/US2008/085213 completed Mar. 25, 2009, and mailed on Mar. 31, 2009.

*Primary Examiner*—Edward J Glick
*Assistant Examiner*—Thomas R Artman
(74) *Attorney, Agent, or Firm*—Jeffrey Klembczyk, Esq.; Kevin P. Radigan, Esq.; Heslin Rothenberg Farley & Mesiti P.C.

(57) ABSTRACT

A sample cell insertion and removal apparatus for an analysis instrument, including a horizontally sliding frame; a sample cell carriage movably mounted to the sliding frame, the sample cell carriage including an area to hold a sample cell; wherein upon sliding into and out of the instrument, the sample cell carriage is moved horizontally and vertically into and out of an analysis position. This instrument may include a radiation shielded enclosure into and out of which the apparatus slides, and an x-ray analysis engine which transmits x-rays upwards towards the sample cell which projects from a bottom of the apparatus. The disclosed sample cell is especially suited for an x-ray analysis engine having a focal spot requiring alignment with the sample in the sample cell.

15 Claims, 11 Drawing Sheets

10
2B
12
22
110
22
17
2B
24
18
16
100
20
24

12
22
22
14
13
24
24

U.S. PATENT DOCUMENTS 6,108,398 A * 8/2000 Mazor et al. .................. 378/45
6,111,930 A * 8/2000 Schipper ...................... 378/79
6,381,303 B1 * 4/2002 Vu et al. ....................... 378/46
6,603,544 B1 * 8/2003 Eckert ........................ 356/246
6,902,703 B2 * 6/2005 Marquiss et al. ............ 422/100
7,342,995 B2 * 3/2008 Sato et al. ..................... 378/46
7,729,471 B2 * 6/2010 Burdett et al. ................ 378/47
2001/0048899 A1 12/2001 Marouiss
2003/0142781 A1 * 7/2003 Kawahara et al. ............. 378/44
2009/0155823 A1 * 6/2009 Bunce et al. ............... 435/7.92

* cited by examiner

SLIDING SAMPLE CELL INSERTION AND REMOVAL APPARATUS FOR X-RAY ANALYZER

CROSS-REFERENCE TO RELATED PATENT

This application claims the benefit of U.S. provisional patent application Ser. No. 61/005,213, filed Dec. 3, 2007, which is hereby incorporated herein by reference in its entirety.

TECHNICAL FIELD

This invention relates in general to sample handling for sample analysis, and in particular to a precision insertion and removal device in the form of a sliding drawer to present a sample cell accurately to an x-ray analyzer where minimization of x-ray leakage and precise positioning are required.

BACKGROUND OF THE INVENTION

X-ray analysis of samples is a growing area of interest across many industries such as medical, pharmaceutical, and petroleum. U.S. Pat. Nos. 6,934,359 and 7,072,439, incorporated by reference herein in their entirety and assigned to X-Ray Optical Systems, Inc., the assignee of the present invention, disclose monochromatic wavelength dispersive x-ray fluorescence (MWD XRF) techniques and systems for the analysis of liquid samples. As one particular example, these patents disclose techniques for the determination of the level of sulfur in petroleum fuels, and a commercialized analyzer (SINDIE) is now in widespread use for this measurement at petroleum refining, pipeline, and terminal facilities.

Sample handling is of critical importance in such systems, as is x-ray shielding. It is a general requirement of bench-top x-ray analysis systems to minimize x-ray exposure during sample loading and unloading. Traditionally, this is accomplished by interlock systems which mechanically and/or electrically control an x-ray blocking "shutter" mechanism over the x-ray source. The interlock system senses an operator opening the system to load/unload a sample, and automatically activates the shutter to completely block any x-rays from transmitting through the now-open sample door, toward an operator. Implementation of shutter mechanisms can be complex and costly, therefore, there is a need for a sample insertion and removal system which simplifies the x-ray interlock and/or shutter requirements.

Moreover, any sample insertion and removal technique must also present the sample to the x-ray measurement engine at a precise distance (along a z-axis as discussed below) for proper alignment to the requisite x-ray analysis spot. This z-axis alignment is critically important for x-ray optic enabled analyzers (such as those disclosed in the above-incorporated U.S. Patents and discussed further below) because of the sensitivity of the measurement to the focal spots of one or two separate optics in the x-ray excitation and/or detection paths.

Finally, it is important to minimize operator interference with the internal measurement areas of the analyzer, when inserting and removing samples.

What is required, therefore, is a sample insertion and removal apparatus, which minimizes x-ray leakage and simplifies x-ray shutter design, which provides precise alignment of a sample to an x-ray analyzer engine, especially an x-ray optic-enabled analyzer engine, and which protects delicate internal measurement components from operators during regular use of the analyzer.

SUMMARY OF THE INVENTION

The shortcomings of the prior art are overcome and additional advantages are provided by the present invention which in one aspect is a sample cell insertion and removal apparatus for an analysis instrument, including a horizontally sliding frame; a sample cell carriage movably mounted to the sliding frame, the sample cell carriage including an area to hold a sample cell; wherein upon sliding into and out of the instrument, the sample cell carriage is moved horizontally and vertically into and out of an analysis position. This instrument may include a radiation shielded enclosure into and out of which the apparatus slides, and an x-ray analysis engine which transmits x-rays upwards towards the sample cell which projects from a bottom of the apparatus. The disclosed sample cell is especially suited for an x-ray analysis engine having a focal spot requiring alignment with the sample in the sample cell.

Further additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in connection with the accompanying drawings in which:

DETAILED DESCRIPTION OF THE INVENTION

Figure 1A:
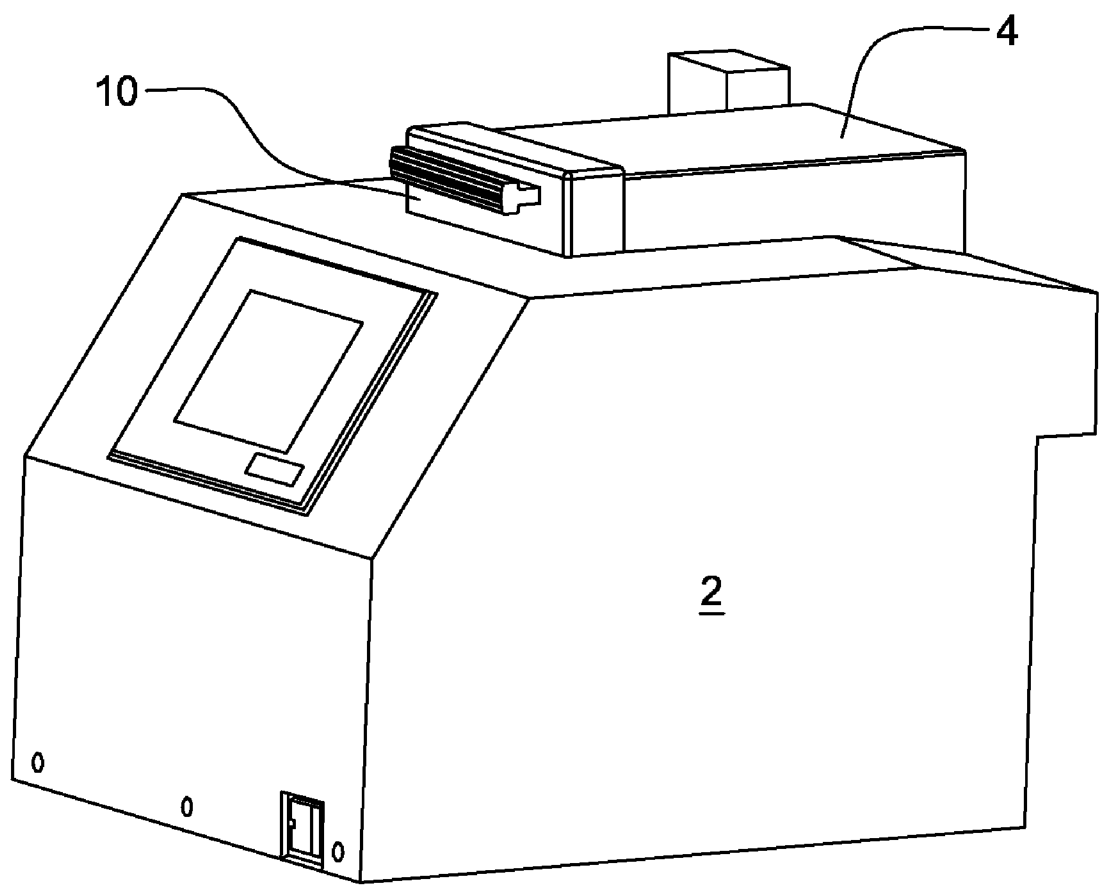
FIG. 1*a* is a perspective view of an x-ray analysis instrument incorporating a sliding sample drawer assembly in accordance with one aspect of the present invention.

In accordance with the present invention, and with reference to FIG 1*a*, an x-ray analyzer 2 includes a sliding sample drawer 10 within a shielded enclosure 4. As discussed further below, the sample drawer opens horizontally, allowing operator access to a sample cell. When either in its open or closed position, the shielded enclosure 4 provides shielding for x-rays being transmitted upward in a vertical direction from an x-ray analysis engine within analyzer 2. This constant level of shielding, regardless of the position of the sample drawer, can decrease the complexity of the requisite x-ray shielding, interlock, and shuttering mechanisms normally required when samples are inserted and/or removed from x-ray analyzers.

Figure 1B:
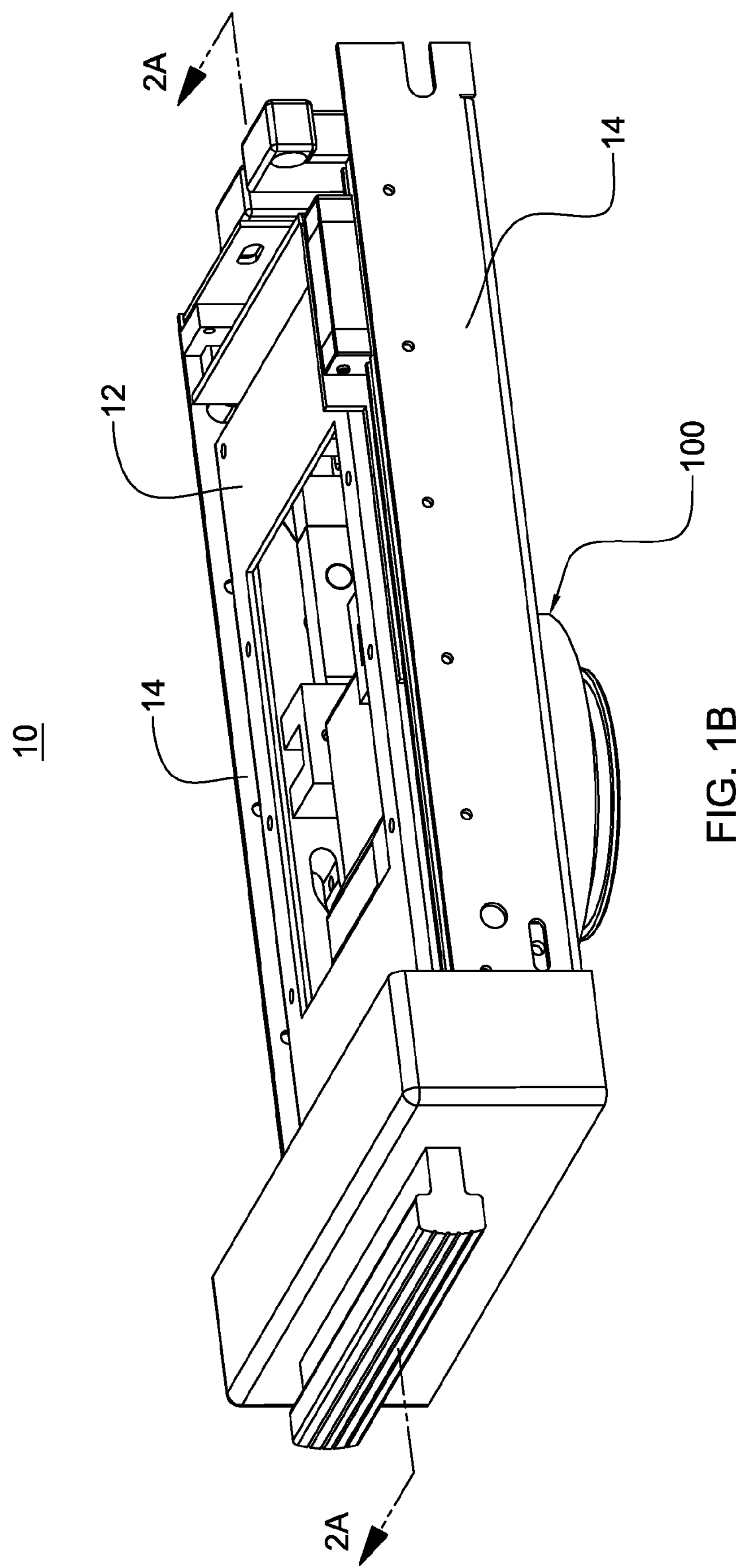
FIG. 1*b* is a perspective view of the drawer assembly of FIG. 1*a;*

FIG. 1*b* is an isometric view of certain features of the sample drawer assembly 10 in accordance with the present invention. Though not part of the sample drawer, the outlines of an x-ray analysis engine 100 are shown under the drawer, to provide a relative positional and operational index for the drawer. Drawer assembly 2 includes runners 14 (for attachment to the analyzer frame, not shown) and an interior frame 12 as discussed further below.

Figure 2A:
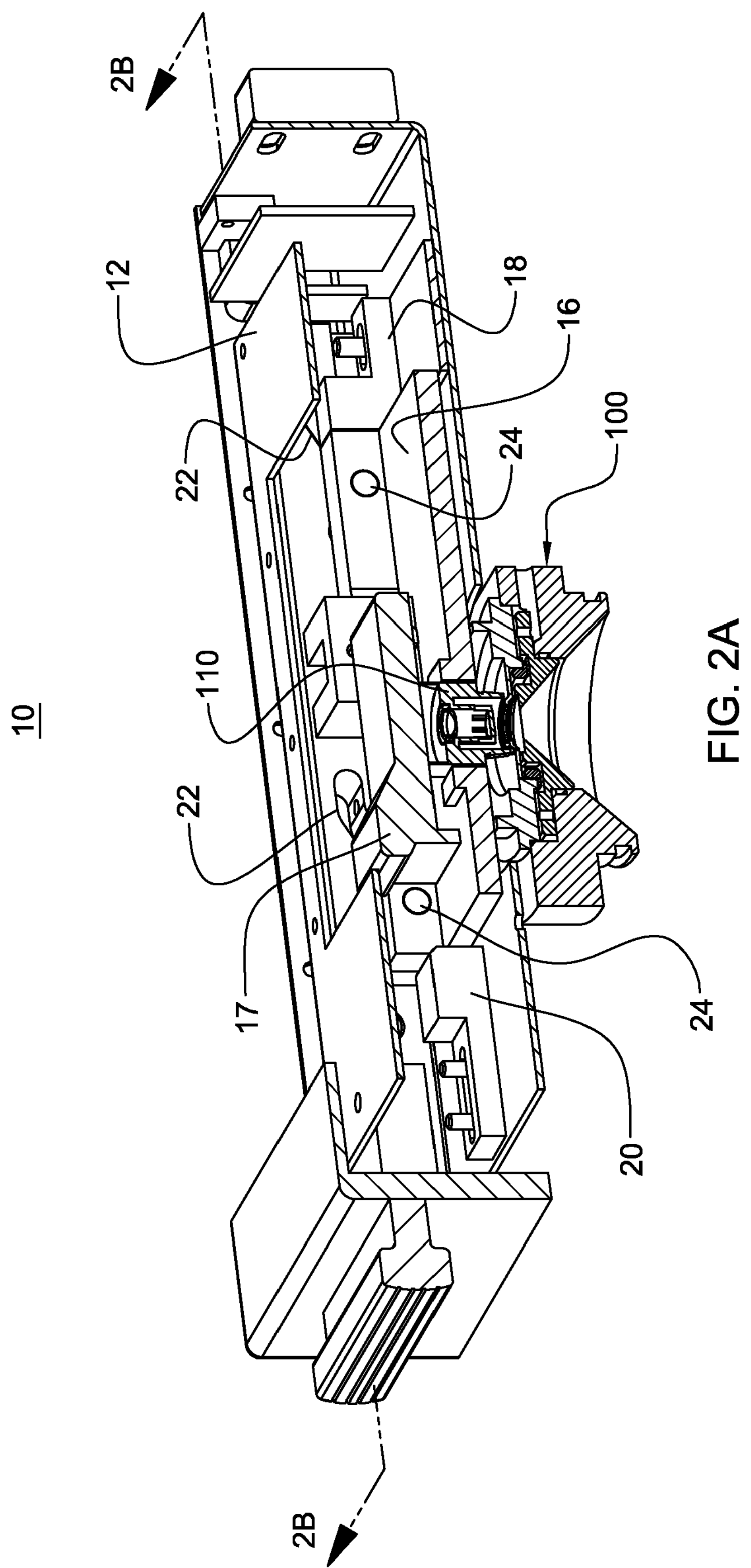
FIGS. 2*a-b* are sectional views of the drawer assembly in a fully closed position with the sample cell fully vertically engaged with the x-ray analysis engine.

FIG. 2*a* is a sectional view of FIG. 1*b*, showing additional interior detail and sample placement. More particularly, drawer assembly 10 is shown in a fully closed position with a sample cell 110 fully, vertically engaged with the x-ray analysis engine 100. As discussed further below, sample cell 110 includes an x-ray transparent film upon which the cell is positioned. This ensures proper z-axis alignment of the sample to an optic-enabled analysis engine. A movable carriage 16 ensures precise placement of cell 110 onto engine 100. Sample cell 110 is positioned within a movable carriage 16, movably held within frame 12—which is slidably engaged to runners 14. In this position, carriage 16 is vertically positioned between the space defined by rear block 18 and forward block 20, which, as discussed below, operate to engage a cam/slot (24/22) placement mechanism on frame 12, which in turn ensures that carriage 16 (holding sample cell 110) gracefully and precisely drops into, and rises out of, its analysis position shown in this FIG. 2*a*. A hinged radiation blocking lid 17 can also be provided over the sample cell 110 to further shield the operator and environment from radiation.

Figure 2B:
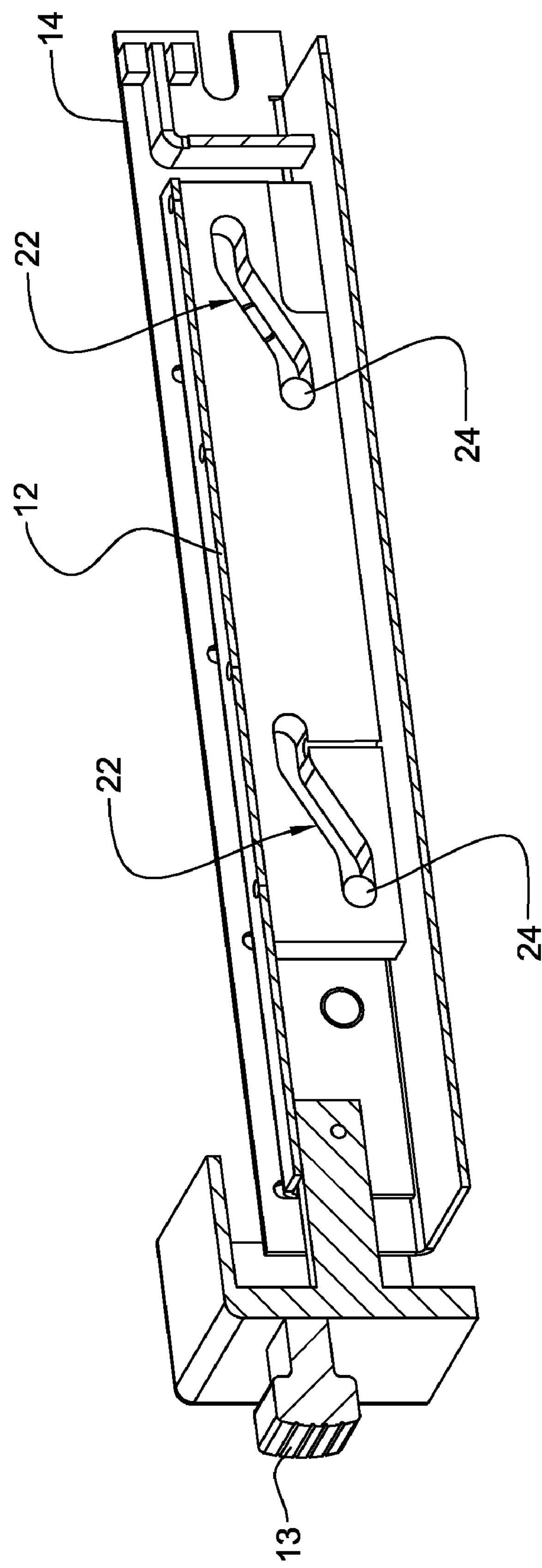

FIG. 2*b* is a further sectional view of the drawer assembly of FIG. 2*a*, showing additional detail of the cam/slot system discussed above. Interior frame 12 is fixedly attached to drawer handle 13. Frame 12 includes slots 22 having upper and lower positions into which cams 24 of carriage 16 are guided when sliding frame 12 horizontally into/out of the analyzer. In this figure, cams 24 are in their lower position, corresponding to the fully lowered "analysis" position for sample cell 110, shown in FIG. 2*a*.

Figure 3A:
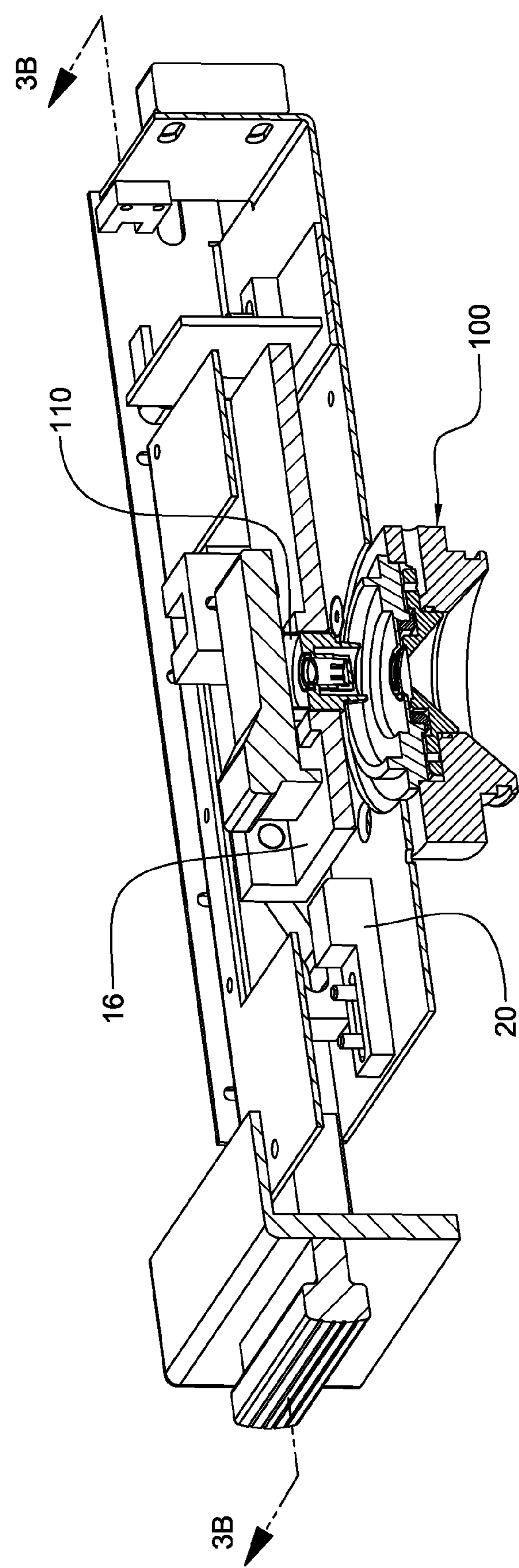
FIGS. 3*a-b* are sectional views of the drawer assembly in a partially closed position with the sample cell vertically disengaged from the x-ray analysis engine.
Figure 3B:
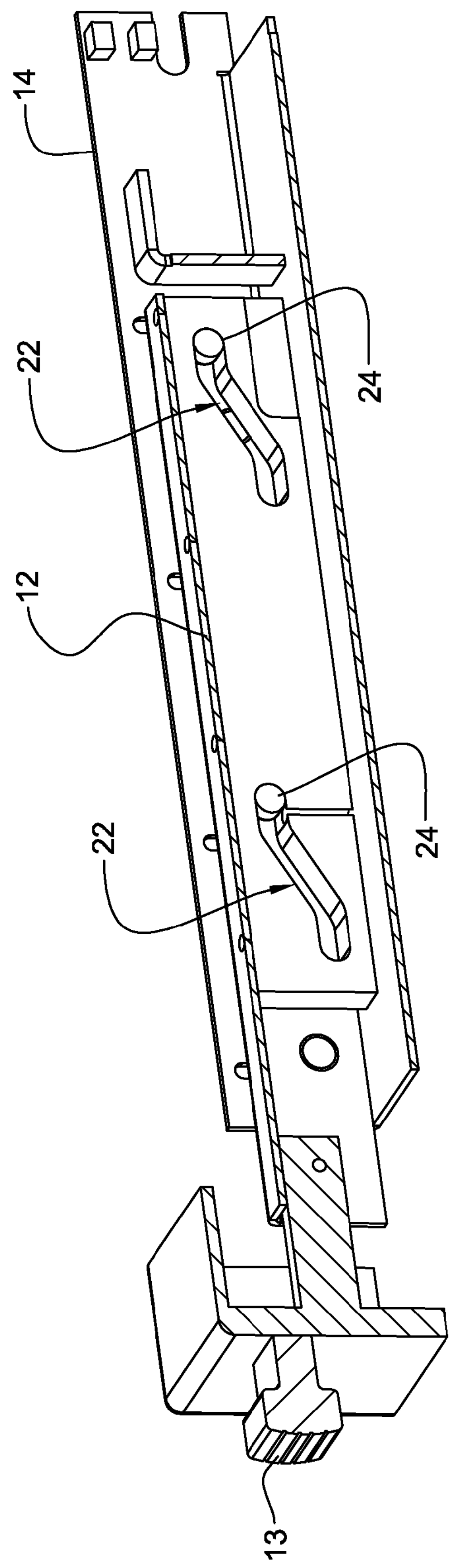

FIGS. 3*a-b* show the drawer assembly in a closed position, but with carriage 16 with sample cell 110 raised out of their analysis position (of FIGS. 2*a* -2*b*) and ready to be completely moved out of the analyzer for operator access. Here (FIG. 3*b*) cams 24 have been guided into the upper areas of slots 22, by the opposing force exerted upon the carriage by forward block 20 as the drawer handle 13 is pulled.

Figure 4A:
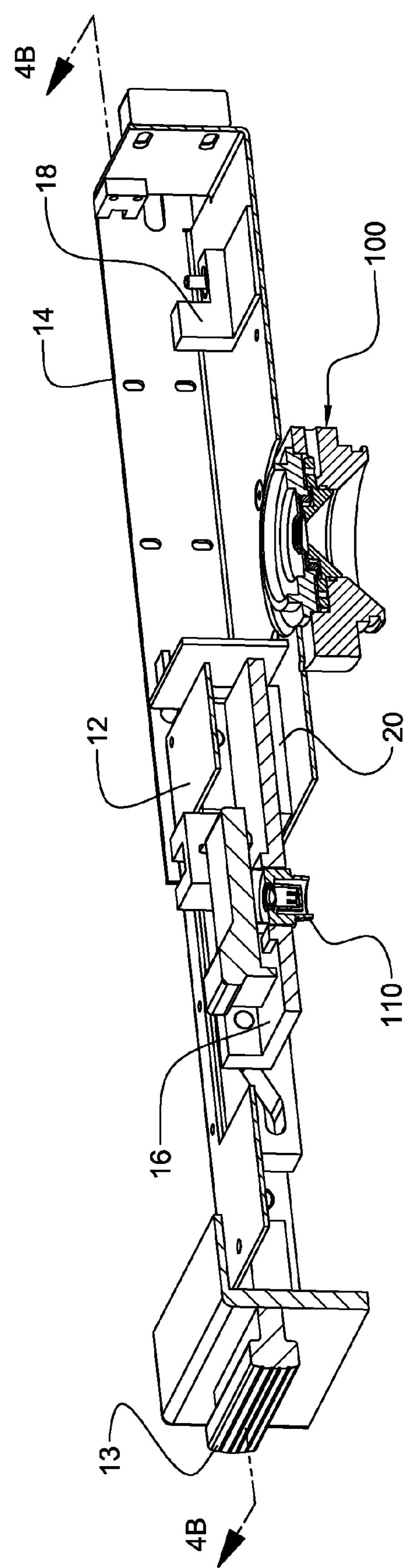
FIGS. 4*a-b* are sectional views of the drawer assembly in an open position with the sample cell available to a user.
Figure 4B:
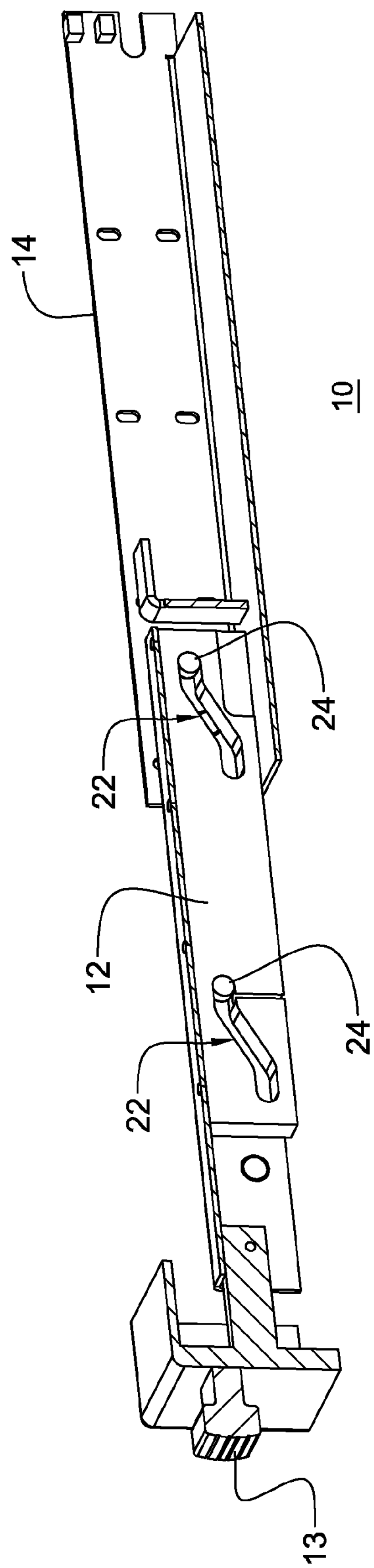

Finally, FIGS. 4*a-b* show the sample drawer assembly in its fully open position, where the sample cell 110 can be removed/dropped in with ease by the operator. Here, the carriage has risen above the rounded top surface (not shown) of forward block 20 and is carried out of the instrument smoothly in frame 12. Cams 24 have remained in the upper area of slots 22, which provide the leftward force to move the carriage to the left and out of the analyzer. Notably, even in this fully open position, any x-ray transmission from x-ray engine 100 is minimized by the shielded enclosure 4; and, the internal measurement mechanisms of the x-ray analyzer (i.e., engine windows), remain inaccessible to a routine operator who may be inserting and removing samples.

Figure 5A:
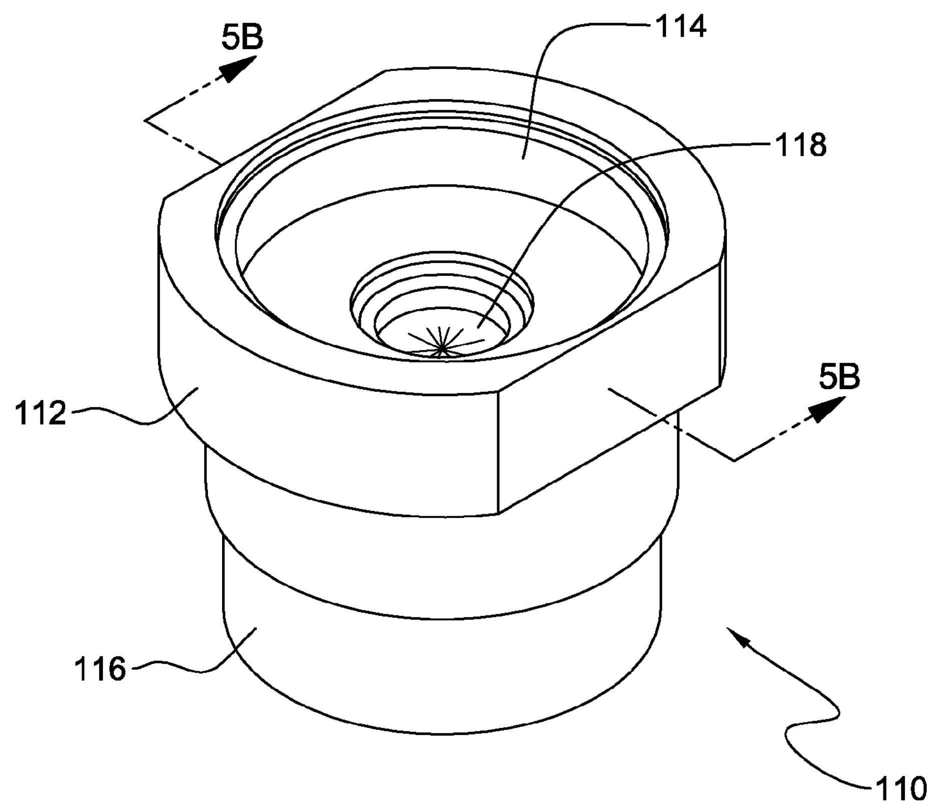
FIGS. 5*a-b* are an isometric and sectional view, respectively, of an exemplary sample cup useable in the present invention.
Figure 5B:
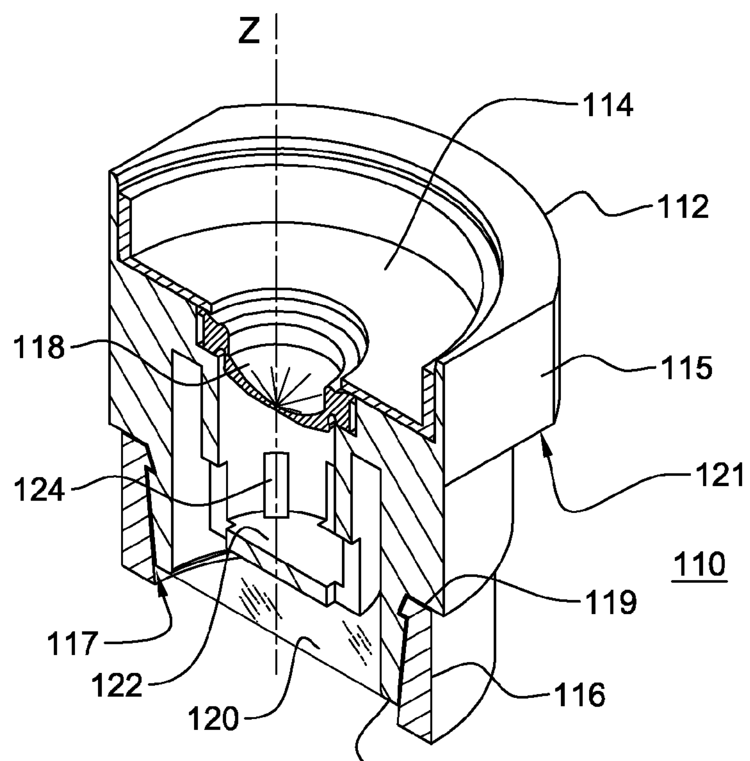

Exemplary Sample Cells:

The sample cell discussed above is disclosed in the previously filed, U.S. patent applications entitled PRE-FILMED PRECISION SAMPLE CELL FOR X-RAY ANALYZER, U.S. Ser. No.: 60/991,396, filed on Nov. 30, 2007, and U.S. Ser. No. 12/323,590, filed on Nov. 26, 2008, each of which is incorporated by reference herein in its entirety. Summarizing a first embodiment of the sample cell, and with reference to FIGS. 5*a-b* (where like elements are referred to using like element numbers), a pre-filmed, precision sample cell 110 is provided. The sample cell includes an outer body 112 forming an interior sample reservoir, an upper end of which includes a fill valve 18 held in place by an exemplary friction-fitted cap 114.

The fill valve is preferably directional, i.e., 1-way to allow a sample in (via a pipette or other insertion device), but preventing a sample from leaking out. The SUREFLO or MEDIFLO directional elastomeric valves available from Liquid Molding Systems, Inc. are examples of such directional valves. Such valves can also be designed/chosen to provide an adequate venting capability of the sample reservoir in one embodiment.

The lower end of the interior sample reservoir is formed of a film 120 (e.g., mylar) which can be wrapped tightly around the lower ends 113 of the body 112, and held in place using a conformal ring. Other attachment techniques are possible, including glues, ultrasonic, RF, or other heating techniques to create a bond between the film and the body around the perimeter of the lower ends 113. The film is preferably designed with enough strength to hold the sample (and, as discussed further below, with enough strength to support the entire sample cell in the instrument), while allowing penetration of x-rays, and resultant x-ray fluorescence to/from the x-ray analysis engine. The sample can be a liquid sample, a partially-liquid sample, or a solid (e.g., powder) sample.

Film 120 may be fastened in place around the lower edge 113 of the body 112 using a conformal ring 116. In one embodiment, the ring snaps into place using barbed-shaped edges which mate with complimentary surfaces in region 119, or another snapping technique which provides an essentially permanent fit to discourage or prevent disassembly. In accordance with this aspect of the present invention, friction-fit cap 114, and/or snapping ring 116, are designed to be essentially, permanently, mounted on the body 112. This permanent mounting can be effected using friction for the cap 114, and 1-way barbs 119 for ring 116. Such permanent mounting (i.e., at a precision assembly facility) ensures that the fill valve is precisely placed, and/or the film is precisely mounted. This precise, factory-set mounting ensures precision placement, discourages tampering in the field, while allowing some level of component interchangeability, including the ability to use cut pieces of film purchased in volume, and different types of films or fill valves.

In one embodiment, an edge of the ring 116 extends beyond the lower end 113 of the body over which the film is fastened forming a recessed area 117. The sample cell can then rest upon the lower edge of ring 116, when placed on a surface, with the film being separated from the surface by a distance corresponding to the depth of the recess. This prevents contamination of the outer surface of the film 120 when the sample cell is in use.

A blocking structure 122 can also be provided within the reservoir to prevent an inserted pipette from puncturing the film 120, while allowing the sample to circulate within the reservoir. Apertures 124 in the blocking structure 122 can also be used to selectively pass certain sized particulates to the analysis area near the film.

Other features include a horizontal edge 121 which can assist/control the vertical placement of the cell in an x-ray analysis engine; and opposing faces 115 which can also be used to assist/control the horizontal/rotational placement of the cell. The precise size and film fastening of the sample cell allow for precise placement of the sample along the Z axis which, as discussed above, is critical for x-ray analysis systems.

The body and other parts discussed above can be formed using injection molding of a high density, polyethylene (HDPE) compound.

Figure 6A:
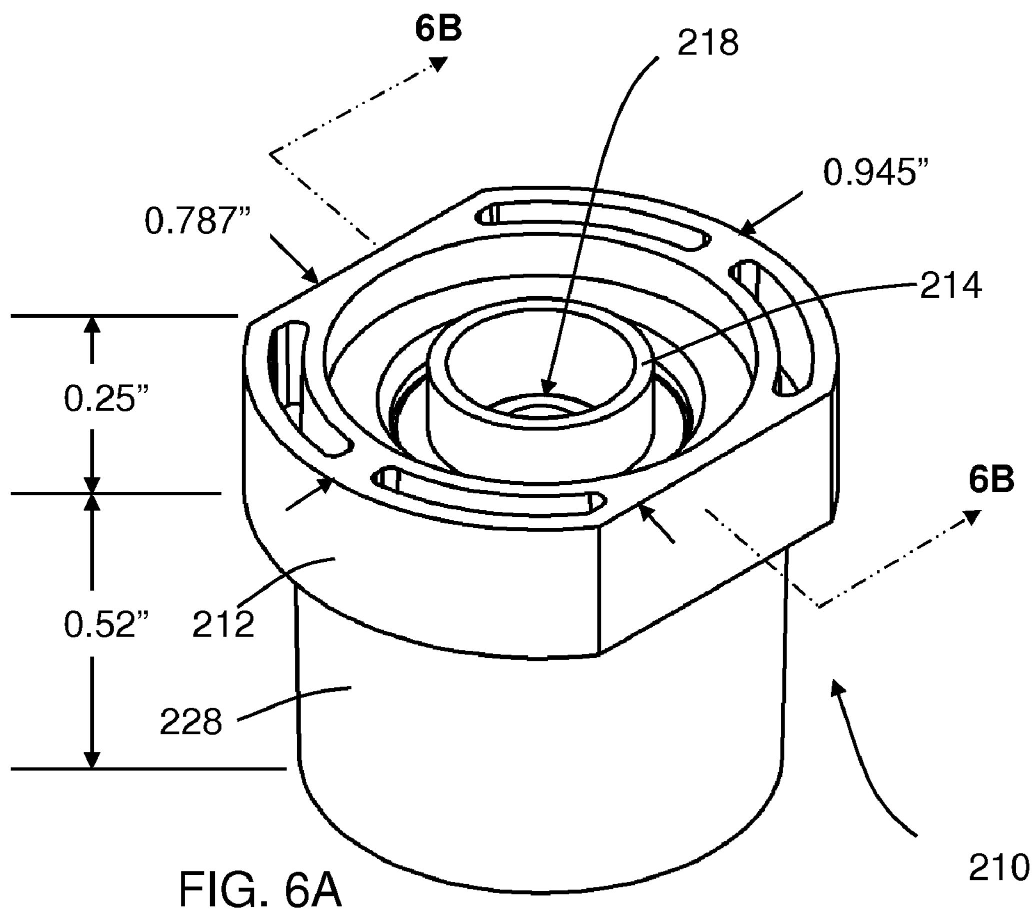
FIGS. 6*a-b* are an isometric and sectional view, respectively, of another exemplary sample cup useable in the present invention.
Figure 6B:
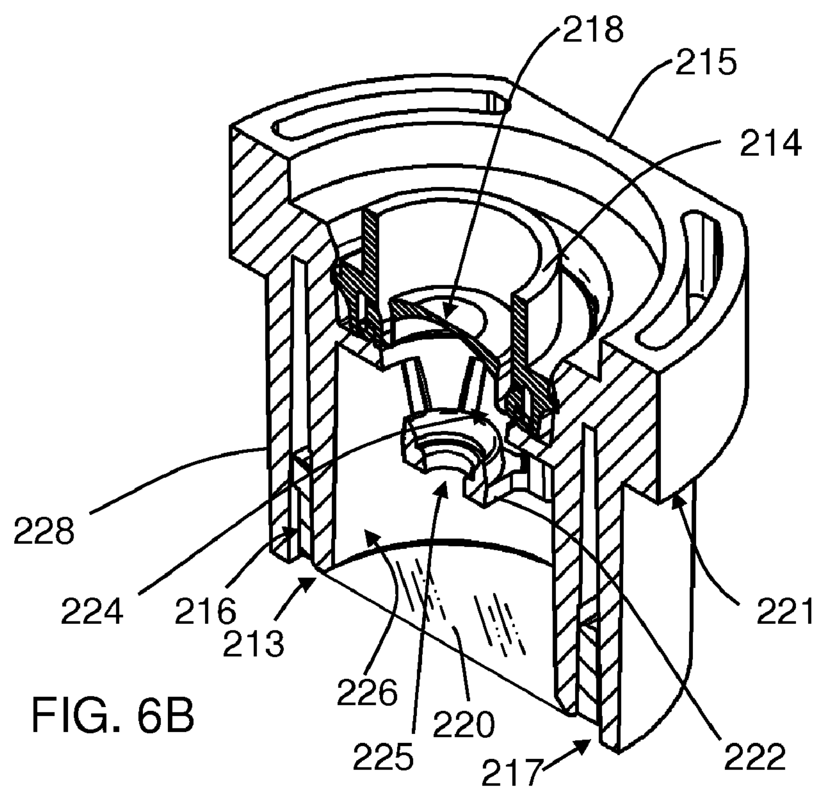

In accordance with another embodiment of the sample cell, and with reference to FIGS. 6*a-b* (where like elements are referred to using like element numbers), a pre-filmed, precision sample cell 210 is provided. The sample cell includes an outer body 212 forming an interior sample reservoir, an upper end of which includes a fill valve 218 held in place by an exemplary snap-in cap 214.

The fill valve is preferably directional, i.e., 1-way to allow a sample in (via a pipette or other insertion device), but preventing a sample from leaking out. The SUREFLO or MEDIFLO directional elastomeric valves available from Liquid Molding Systems, Inc. are examples of such directional valves. Such valves can also be designed/chosen to provide an adequate venting capability of the sample reservoir in one embodiment.

The lower end of the interior sample reservoir is formed of a film 220 (e.g., mylar) which can be wrapped tightly around a certain lower edge 213 of the body 212, and held in place using a conformal ring 216. Other attachment techniques are possible, including glues, ultrasonic, RF, or other heating techniques to create a bond between the film and the body around the perimeter of the lower edges 213. The film is preferably designed with enough strength to hold the sample (and, as discussed further below, with enough strength to support the entire sample cell in the instrument), while allowing penetration of x-rays, and resultant x-ray fluorescence to/from the x-ray analysis engine. The sample can be a liquid sample, a partially-liquid sample, or a solid (e.g., powder) sample.

Film 220 may be fastened in place around the lower edge 213 of the body 212 using a conformal ring 216. In one embodiment, the ring 216 is frictionally held in place between an outer wall 228 and an inner wall 226 formed, e.g. as integral parts of the body 212. This method provides an essentially permanent fit to discourage or prevent disassembly, with ring 216 pushed into the cylindrical cavity formed between walls 226 and 228. In accordance with this aspect of the present invention, snap-in cap 214, and/or friction ring 216, are designed to be essentially, permanently, mounted on the body 212. Permanent mounting for cap 214 can be effected using 1-way barbs where one side of the snap-in cap 214 has a barbed-shape edge which mates with the complimentary structure of the body. Permanent mounting for the ring 216 can be effected using friction between the ring and the inner and/or outer walls. Such permanent mounting (i.e., at a precision assembly facility) ensures that the fill valve is precisely placed, and/or the film is precisely mounted. This precise, factory-set mounting ensures precision placement, discourages tampering in the field, while allowing some level of component interchangeability, including the ability to use cut pieces of film purchased in volume, and different types of films or fill valves.

In accordance with another aspect of the present invention, the lower edge of outer wall 228 extends beyond the lower edge of 213 of inner wall 226 over which the film is fastened, thereby forming a recessed area 217. The sample cell can then rest upon the outer wall 228 when placed on a surface, with the film being separated from the surface by a distance corresponding to the depth of the recess. This prevents contamination of the outer surface of the film 220 when the sample cell is in use.

A blocking structure 222 can also be provided within the reservoir to prevent an inserted pipette from puncturing the film 220, while allowing the sample to circulate within the reservoir. Apertures 224 in the blocking structure 222 can also be used to selectively pass certain sized particulates to the analysis area near the film. One aperture, e.g., a hole 225, is provided at the bottom of blocking structure 222 and is large enough to allow the sample to pass through to the film without upward splatter, but small enough to prevent the pipette from passing through and puncturing the film.

Other features include a horizontal edge 221 which can assist/control the vertical placement of the cell in an x-ray analysis engine; and opposing faces 215 which can also be used to assist/control the horizontal/rotational placement of the cell. The precise size and film fastening of the present invention allow for precise placement of the sample along the Z axis which, as discussed above, is critical for x-ray analysis systems.

Certain exemplary dimensions are shown in FIGS. 6*a-b*; which convey the rather small size of the sample cell of the present invention in comparison to the known approaches. The overall height of the sample cell is less than about 0.8 inches, and the outer diameter is less than about 1.0 inch. In general, variations of about +/− 25% from the depicted dimensions are considered to fall within the principles of the present invention.

Those skilled in the art will recognize that any combination of the features of the first (FIGS. 5*a-b*) and second (FIGS. 6*a-b*) embodiments of the sample cell can be combined without departing from the principles of the present invention.

Figure 7:
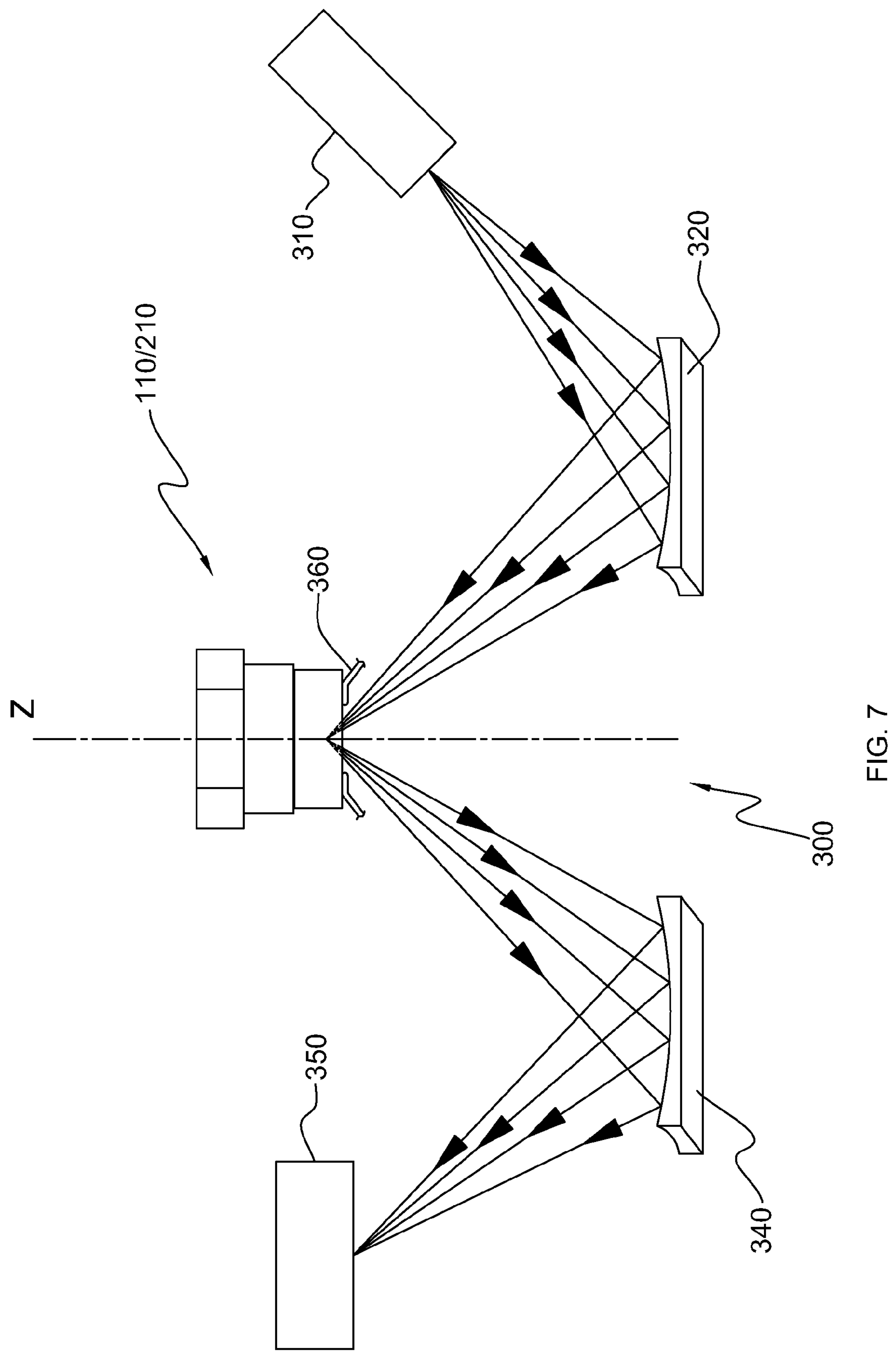
FIG. 7 is a schematic view of the sample cell aligned to a focal spot of an x-ray optic-enabled x-ray analysis engine, according to another aspect of the present invention.

Exemplary MWD XRF X-Ray Analysis System:

FIG. 7 depicts in schematic view an exemplary MWD XRF x-ray analysis engine 300 in combination with the sample cell 110/210, and to which the present insertion and removal apparatus may also be directed. The x-ray analysis engine has a focal spot requiring alignment with the sample in the sample cell. Engine 300 includes, in one embodiment, an x-ray source 310 and detector 350. X-ray optics 320 and/or 340 can be placed in the excitation and/or detection paths of the engine. These optics require a high degree of alignment with the sample spot to function at the requisite limits of detection discussed above. Such optics include, for example, curved crystal monochromating optics such as those disclosed in commonly assigned U.S. Pat. Nos. 6,285,506; 6,317,483; and 7,035,374; and/or multilayer optics such as those disclosed in commonly assigned U.S. patent application entitled "X-Ray Focusing Optic Having Multiple Layers With Respective Crystal Orientations," U.S. Ser. No. 11/941,377 filed Nov. 16, 2007; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506 and 7,209,545 are also useable. Each of the above-noted patents and patent applications is incorporated herein by reference in its entirety.

Curved monochromating optics in the excitation and detection path is shown in FIG. 7, which is the configuration of the SINDIE sulfur analyzer discussed above. However, an optic may only be present in one of these paths, which still requires precise alignment. In one example, an optic of any of the above-describe types may only be present in the excitation path, and the detection path would include an energy dispersive detector. This is the common configuration of an energy dispersive x-ray fluorescence (EDXRF) system.

In one embodiment, to ensure precision alignment of the sample to the focal spot, the sample cell could rest on one or more supports 360 which directly contact the film. The upper surfaces (not visible) of the supports are positioned in the instrument to correspond to the focal spot, and when the film surface rests on the supports, precise alignment is ensured.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. A sample cell insertion and removal apparatus, in combination with a sample cell, for an x-ray analysis instrument, the apparatus comprising:

a horizontally sliding frame; and a sample cell carriage movably mounted to the sliding frame, the sample cell carriage including an area to hold a sample cell;

wherein upon sliding into and out of the instrument, the sample cell carriage is moved horizontally and vertically into and out of an analysis position;

wherein the sample cell comprises:

an outer body forming a sample reservoir therein;

a directional fill valve disposed in an upper end of the outer body and forming an upper end of the sample reservoir, the fill valve for accepting a sample during filling, and preventing sample leakage while providing venting after filling; and a film covering a lower edge of the outer body, and forming a bottom end of the sample reservoir, the film for presenting the sample to an analysis focal spot of the x-ray analysis instrument.

2. The combination of claim 1, wherein the frame and the carriage include means to move the sample cell into and out of the analysis position.

3. The combination of claim 2, wherein the means to move includes a system of cams, and slots through which the cams are guided.

4. An x-ray analysis instrument in further combination with the combination of claim 1, the instrument including a radiation shielded enclosure into and out of which the apparatus slides, and an x-ray analysis engine which transmits x-rays upwards towards the sample cell which projects from a bottom of the apparatus.

5. The combination of claim 1, further comprising a ring for fixedly fastening the film around the lower edge of the body, which upon fastening remains around the lower edge of the body over the film.

6. The combination of claim 5, wherein an edge of the ring extends beyond the lower end of the body over which the film is fastened, upon which the sample cell can rest when placed on a surface, the film being thereby separated from the surface by a distance corresponding to the size of the extension.

7. The combination of claim 5, wherein the outer body includes an inner wall and an outer wall between which the ring is frictionally held, and a lower edge of the inner wall comprises the edge around which the film is fastened.

8. The combination of claim 7, wherein the outer wall extends beyond the lower edge of the inner wall over which the film is fastened, upon which the sample cell can rest when placed on a surface, the film being thereby separated from the surface by a distance corresponding to the size of the extension.

9. An x-ray analysis engine in further combination with the combination of claim 1, the x-ray analysis engine having an x-ray focal spot requiring alignment with the sample in the sample cell insertion and removal apparatus.

10. The combination of claim 9, further comprising at least one x-ray optic disposed in an x-ray excitation and/or detection path, requiring alignment to the focal spot.

11. The combination of claim 10, wherein the at least one x-ray optic comprises a curved monochromating optic or a polycapillary optic.

12. The combination of claim 10, wherein the x-ray analysis engine comprises a WDXRF analysis engine having a monochromating optic in the detection path.

13. The combination of claim 12, wherein the analysis instrument is a sulfur analysis instrument.

14. The combination of claim 10, wherein the x-ray analysis engine comprises an EDXRF analysis engine having the at least one optic in the excitation path and an energy dispersive detector in the detection path.

15. The combination of claim 10, wherein the sample cell in the sample cell insertion and removal apparatus is supported by the film in said combination using supports contacting the film of the sample cell, thereby ensuring alignment of the sample to the focal spot.

* * * * *